(12) United States Patent
Lochead et al.

(10) Patent No.: US 6,184,229 B1
(45) Date of Patent: Feb. 6, 2001

(54) 6-PYRROLIDIN-2-YLPYRINDINE DERIVATIVES, THEIR PREPARATION AND APPLICATION IN THERAPY

(75) Inventors: Alistair Lochead, Charenton; Samir Jegham, Montferrier-sur-Lez; Frédéric Galli, Vaucresson, all of (FR)

(73) Assignee: Sanofi-Synthelabo, Paris (FR)

( * ) Notice: Under 35 U.S.C. 154(b), the term of this patent shall be extended for 0 days.

(21) Appl. No.: 09/462,352

(22) PCT Filed: Jul. 7, 1998

(86) PCT No.: PCT/FR98/01446

§ 371 Date: Jan. 7, 2000

§ 102(e) Date: Jan. 7, 2000

(87) PCT Pub. No.: WO99/02517

PCT Pub. Date: Jan. 21, 1999

(51) Int. Cl.[7] .................. A61K 31/435; C07D 401/04
(52) U.S. Cl. ................. 514/299; 546/112; 546/183
(58) Field of Search ............... 514/299; 546/112, 546/183

(56) References Cited

U.S. PATENT DOCUMENTS

| | | | |
|---|---|---|---|
| 5,227,391 | 7/1993 | Caldwell et al. | 514/343 |
| 5,232,933 | 8/1993 | Lippiello et al. | 514/343 |

OTHER PUBLICATIONS

N.D. Cosford et al., "(S)–(–)–5–Ethynyl–3–(1–methyl–2–pyrrolidinyl)pyridine Maleate (SIB–1508Y): A Novel Anti–Parkinsonian Agent with Selectivity for Neuronal Nicotinic Acetylcholine Receptors", Journal of Medicinal Chemistry, vol. 39, No. 17, pp. 3235–3237, (1996).

*Primary Examiner*—C. S. Aulakh
(74) *Attorney, Agent, or Firm*—Finnegan, Henderson, Farabow, Garrett & Dunner, L.L.P.

(57) ABSTRACT

Compound corresponding to the general formula (I)

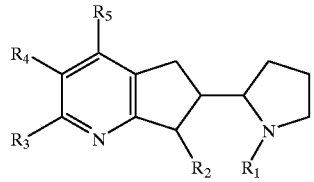

(I)

in which $R_1$ represents a hydrogen atom, a $(C_1-C_4)$alkyl group or a phenyl$(C_1-C_4)$alkyl group, $R_2$ represents a hydrogen atom or a $(C_1-C_4)$ alkyl group, and $R_3$, $R_4$ and $R_5$ each represent a hydrogen or halogen atom or a trifluoromethyl, cyano, hydroxyl, $(C_1-C_6)$alkyl or $(C_1-C_6)$alkoxy group.

10 Claims, No Drawings

6-PYRROLIDIN-2-YLPYRINDINE DERIVATIVES, THEIR PREPARATION AND APPLICATION IN THERAPY

This application is a 371 of PCT/FR98/01446 filed Jul. 07, 1998, now WO 99/02517 published Jan. 21, 1999.

The present invention relates to the compounds of general formula (I)

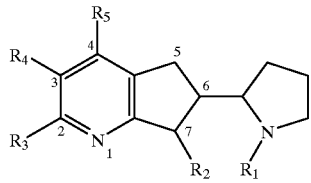

in which
$R_1$ represents a hydrogen atom, a $(C_1-C_4)$alkyl group or a phenyl$(C_1-C_4)$alkyl group,
$R_2$ represents a hydrogen atom or a $(C_1-C_4)$ alkyl group, and
$R_3$, $R_4$ and $R_5$ each represent, independently of each other, a hydrogen or halogen atom or a trifluoromethyl, cyano, hydroxyl, $(C_1-C_6)$alkyl or $(C_1-C_6)$alkoxy group.

When $R_2$ represents a hydrogen atom, the molecules of general formula (I) contain two asymmetric carbon atoms, i.e. the carbon atom in position 6 and the carbon atom of the pyrrolidine ring to which it is attached; for the same combination of substituents $R_1$, $R_3$, $R_4$ and $R_5$, the compounds of the invention can thus exist in the form of 4 different isomers.

When $R_2$ is other than a hydrogen atom, the carbon atom in position 7 is also asymmetric; for the same combination of substituents $R_1$, $R_2$, $R_3$, $R_4$ and $R_5$, the compounds of the invention can thus exist in the form of 8 different optical isomers.

The compounds of the invention can also exist in the form of bases or addition salts with acids.

In accordance with the invention, the compounds of general formula (I) can be prepared according to a process illustrated by the scheme which follows.

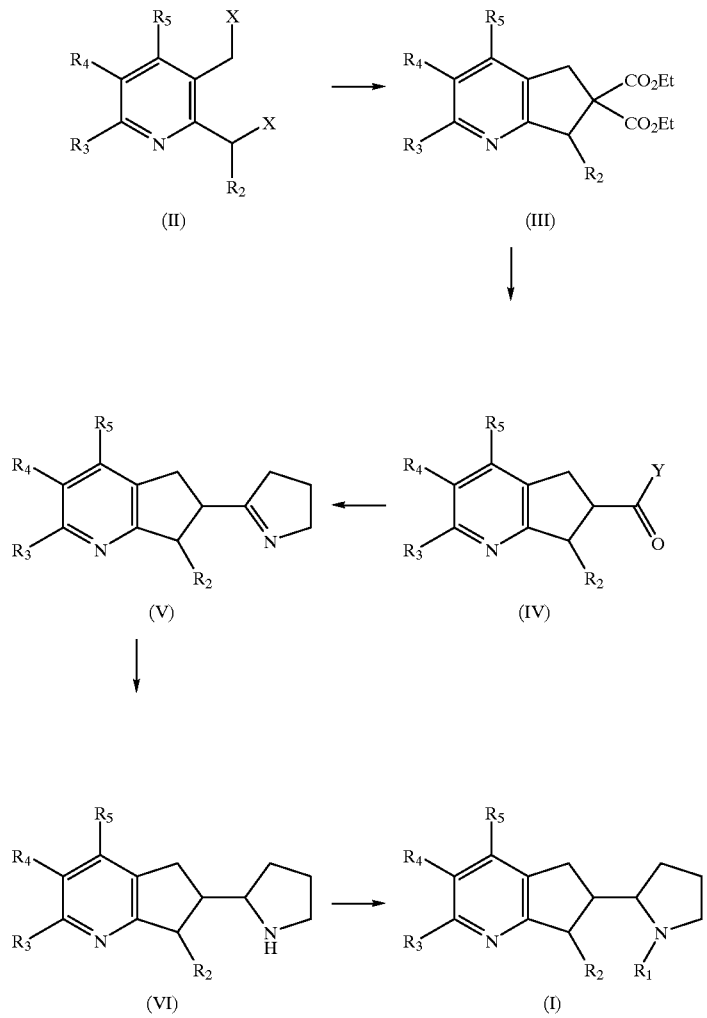

A derivative of general formula (II), in which X represents a halogen atom and $R_2$, $R_3$, $R_4$ and $R_5$ are as defined above, is reacted with diethyl propanedioate in basic medium in order to obtain, via a bis-alkylation, a cyclized diester of general formula (III), which is saponified under acidic conditions, or optionally under basic conditions, into an acid of general formula (IV) in which Y represents a hydroxyl group; this acid can be converted into an ester of general formula (IV) in which Y represents an alkoxy group, or alternatively into a Weinreb amide of general formula (IV) in which Y represents an (N-alkoxy)alkylamino group.

The derivative of general formula (IV) is then treated either according to the method described in *Tetrahedron Lett.*, (1984) 25(46) 5271, or according to the method described in *J. Med. Chem.* (1997) 39 3235. According to the first method, the derivative of general formula (IV) is reacted with the organomagnesium reagent derived from 3-bromopropanamine, in which the amine function is protected with a silyl function, after which this function is hydrolysed in acidic medium; according to the second method, the derivative of general formula (IV) is reacted with N-vinylpyrrolid-2-one under basic conditions in order to form an intermediate which is hydrolysed in acidic medium.

An imine of general formula (V) is obtained, which is reduced to a derivative of general formula (VI) by an agent such as sodium borohydride or sodium cyanoborohydride in a suitable solvent.

The cis and trans stereoisomers formed during this step can be separated by chromatography into more polar isomers and less polar isomers.

If so desired, it is also possible at this stage to separate the enantiomers, for example by treating a cis or trans stereoisomer of general formula (VI) with a chiral substrate, for example an S-proline derivative, under peptide coupling conditions, for example in the presence of dicyclohexylcarbodiimide, in order to obtain a derivative of general formula (I) in which $R_1$ represents a prolinyl group, in the form of a mixture of diastereoisomers which can be separated by chromatography. The enantiomers are then obtained by treating each of the diastereoisomers in acidic medium. Finally, and if it is desired to introduce a group $R_1$ other than a hydrogen atom, an alkylation of the nitrogen in the pyrrolidine ring is carried out by any known method, for example a reductive methylation according to the Eschweiler-Clarck method (formaldehyde and formic acid), or by reductive amination in the presence of an aldehyde and sodium cyanoborohydride, or alternatively by acylation, in order to form an amide, which is reduced to an amine, using an agent such as lithium aluminium hydride.

For certain compounds, all the substituents $R_2$, $R_3$, $R_4$ and $R_5$ cannot be present in the starting compound of general formula (II); depending on their nature, these substituents can be introduced onto one and/or the other of the compounds of general formulae (III), (IV), (V), (VI) and (I), in which $R_2$, $R_3$, $R_4$ and/or $R_5$ represent hydrogen atoms, according to any known methods, for example the method described in *J. Het. Chem.* (1996) 33 1051–1056, optionally after activation of the nitrogen in the pyridine ring by formation of the corresponding N-oxide.

The examples which follow illustrate the preparation of a number of compounds of the invention. The elemental microanalyses and the IR and NMR spectra confirm the structures of the compounds obtained.

The numbers indicated in parentheses in the example titles correspond to those in the 1st column of Table 1 given later.

In the compound names, the hyphen "-" forms part of the name, and the underscore mark "_" serves merely to indicate the line break; it should be removed if a line break does not occur at that point, and should not be replaced either with a normal hyphen or with a space.

EXAMPLE 1

(Compounds Nos. 1 and 2)

Hydrochlorides (2:1) of the isomers of (±)-6-pyrrolidin-2-yl-6,7-dihydro-5H-1-pyrindine.

1.1 Diethyl 6,7-dihydro-5H-1-pyrindine-6,6-dicarboxylate.

3.25 g (0.140 mol) of sodium are dissolved in 200 ml of ethanol in a 500 ml three-necked flask. 7.53 g (0.047 mol) of diethyl malonate are added and the solution is stirred for 5 min. 10 g (0.047 mol) of 2,3-bis(chloromethyl)pyridine (described in *J. Het. Chem.* (1972) 9(4) 843–848) suspended in 150 ml of ethanol are then added and the mixture is refluxed for 6 h.

The mixture is filtered and the filtrate is concentrated under reduced pressure. The residue is taken up in water and extracted with dichloromethane. 11.9 g of product are thus obtained in the form of an oil.

1.2 6,7-Dihydro-5H-1-pyrindine-6-carboxylic acid hydrochloride

A mixture of 9.25 g (0.035 mol) of diethyl 6,7-dihydro-5H-1-pyrindine-6,6-dicarboxylate and 200 ml of concentrated hydrochloric acid is refluxed for 3 h in a 500 ml round-bottomed flask.

The medium is concentrated under reduced pressure and the residue is dried in the presence of phosphorus pentoxide. 5.1 g of product are thus obtained in the form of an amorphous solid.

1.3 N-methoxy-N-methyl-6,7-dihydro-5H-1-pyrindine-6-carboxamide.

9.9 g (49.6 mmol) of 6,7-dihydro-5H-1-pyrindine-6-carboxylic acid hydrochloride dissolved in 120 ml of dimethylformamide are introduced into a 250 ml three-necked round-bottomed flask. 9.65 g (59.5 mmol) of 1,1'-carbonylbis-1H-imidazole are added portionwise and the reaction medium is stirred until the evolution of gas has ceased. 5.8 g (59.5 mmol) of N-methoxymethylamine hydrochloride are added and stirring is continued for 3 h.

The solvent is evaporated off under reduced pressure and the residue is taken up in water and extracted with chloroform. The product is purified by chromatography on silica gel, eluting with a 10/90 mixture of heptane and ethyl acetate. 7.3 g of product are thus obtained in the form of an oil.

1.4 Hydrochlorides of the isomers of (±)-6-pyrrolidin-2-yl-6,7-dihydro-5H-1-pyrindine.

2.06 g (10 mmol) of N-methoxy-N-methyl-6,7-dihydro-5H-1-pyrindine-6-carboxamide dissolved in 100 ml of ether are introduced into a 250 ml three-necked round-bottomed flask, a solution of [lacuna] (30 mmol) of bromo[3-(2,2,5,5-tetramethyl-1-aza-2,5-disilacyclopent-1-yl)propyl] magnesium dissolved in 10 ml of ether is added, at room temperature over 15 min, and the solution is stirred for 15 h. The mixture is cooled to 4° C. and 20 ml of a 3.55 M solution of hydrochloric acid in ethanol is added slowly. The precipitate which forms is collected, taken up in ethanol and stirred for 3 h at room temperature. 6.28 g (100 mmol) of sodium cyanoborohydride are added portionwise, at 4° C., and the mixture is stirred at room temperature for 3 h.

The solvent is evaporated off under reduced pressure and the residue is taken up in water and basified by addition of concentrated sodium hydroxide. The mixture is extracted with chloroform in order to obtain the crude reaction products. The isomers are separated by chromatography on silica gel, eluting with a 95/5/0.5 mixture of chloroform, methanol and aqueous ammonia. 0.65 g of the less polar isomer (referred to hereinbelow as "isomer A") is thus obtained in the form of an amorphous solid which is converted into the hydrochloride (2:1) by the usual method.

Melting point: 228–229° C.,
and 0.27 g of the more polar isomer (referred to hereinbelow as "isomer B") are thus obtained in the form of an amorphous solid which is converted into the hydrochloride (2:1) in the same way.

Melting point: 176–177° C.

EXAMPLE 2
(Compound No. 7)

Hydrochloride (2:1) of (±)-6-(1-methylpyrrolidin-2-yl)-6,7-dihydro-5H-1-pyrindine (derived from isomer A).

A mixture of 0.38 g (1.45 mmol) of the isomer A of (±)-6-pyrrolidin-2-yl-6,7-dihydro-5H-1-pyrindine dissolved in 3.5 ml of formic acid and 3.5 ml of an aqueous 37% formaldehyde solution is heated at 100° C. for 2.5 h in a 25 ml round-bottomed flask.

The mixture is cooled and saturated sodium hydrogencarbonate solution is added. This mixture is extracted with chloroform and the organic phase is dried and evaporated in order to obtain the product in base form. It is converted into the hydrochloride (2:1) by addition of a solution of hydrochloric acid in ethanol. 0.25 g of product is thus obtained.

Melting point: 87–89° C.

EXAMPLE 3
(Compound No. 8)

Fumarate (2:1) of (±)-6-(1-methylpyrrolidin-2-11)-6,7-dihydro-5H-pyrindine (derived from isomer B).

Starting with the most polar isomer obtained during step 1.4, and working according to the method described in Example 2, the final compound is obtained, which is converted into the fumarate (2:1).

Melting point: 116–118° C.

EXAMPLE 4
(Compounds Nos. 3 and 4)

Hydrochlorides (2:1) of the enantiomers of 6-pyrrolidin-2-yl-6,7-dihydro-5H-1-pyrindine (derived from isomer A).

4.1 Ethyl 6,7-dihydro-5H-1-pyrindine-6-carboxylate.

38 g (0.193 mol) of 6,7-dihydro-5H-1-pyrindine-6-carboxylic acid hydrochloride dissolved in 500 ml of ethanol are introduced into a 1 l round-bottomed flask and the solution is refluxed for 24 h.

The reaction medium is cooled, the solvent is evaporated off under reduced pressure, the residue is taken up in water and the aqueous solution is basified by addition of potassium carbonate. This mixture is extracted with chloroform and the solvent is evaporated off. The residue is taken up in a 97/3 mixture of chloroform and methanol and is evaporated under reduced pressure. 15 g of product are thus obtained in the form of an oil.

4.2 Hydrochloride (2:1) of (±)-6-(4,5-dihydro-3H-pyrrol-2-yl)-6,7-dihydro-5H-1-pyrindine.

65.5 ml (130 mmol) of a 2M solution of lithium diisopropylamide in hexane are introduced into a 500 ml three-necked round-bottomed flask under argon. The solution is cooled to −78° C. and 14.56 g (130 mmol) of N-vinylpyrrolidin-2-one dissolved in 100 ml of tetrahydrofuran are added dropwise over 20 min. The solution is stirred for 1 h at −70° C. 25 g (130 mmol) of ethyl 6,7-dihydro-5H-1-pyrindine-6-carboxylate dissolved in 100 ml of tetrahydrofuran are then added and the stirring is continued at room temperature for 20 h.

The solvent is evaporated off under reduced pressure and the residue is taken up in 500 ml of aqueous 6M hydrochloric acid. The solution obtained is refluxed for 4 h and cooled to 4° C. It is basified by addition of concentrated sodium hydroxide and is extracted with chloroform. 18 g of product are thus obtained in the form of an oil.

The hydrochloride (2:1) is obtained by the usual treatment of the base with hydrochloric acid in ethanol.

Melting point: 204–205° C.

4.3 Isomers of (±)-6-pyrrolidin-2-yl-6,7-dihydro-5H-1-pyrindine.

18 g (97 mmol) of (±)-6-(4,5-dihydro-3H-pyrrol-2-yl-6,7-dihydro-5H-1-pyrindine dissolved in 100 ml of methanol in the presence of 11 ml (193 mmol) of acetic acid are introduced into a 250 ml three-necked round-bottomed flask. The mixture is cooled to 4° C. and 4 g (106 mmol) of sodium borohydride are added portionwise. This mixture is stirred at 4° C. for 1 h and hydrolysed by adding 100 ml of water.

The resulting mixture is basified by addition of concentrated sodium hydroxide. This mixture is extracted with chloroform and the solvent is evaporated off. The isomers obtained (A and B) are separated by chromatography on silica gel, eluting with a 90/10/1 mixture of chloroform, methanol and aqueous ammonia. 6.6 g of the less polar isomer (isomer A) and 3.45 g of the more polar isomer (isomer B) are thus obtained.

4.4 Diastereoisomers of (S)-2-(6,7-dihydro-5H-1-pyrindin-6-yl)-1-(pyrrolidin-2-ylcarbonyl)pyrrolidine (derived from isomer A).

6.18 g (32.8 mmol) of the A isomer of (+)-6-pyrrolidin-2-yl-6,7-dihydro-5H-1-pyrindine dissolved in 50 ml of dichloromethane are introduced into a 100 ml three-necked round-bottomed flask at room temperature. 6.77 g (32.8 mmol) of dicyclohexylcarbodiimide and 7.06 g (32.8 mmol) of N-(1,1-dimethylethoxycarbonyl)-(S)-proline are added. A precipitate forms rapidly. The suspension is stirred at room temperature for 1 h.

The precipitate is removed by filtration and the filtrate is treated with 50 ml of trifluoroacetic acid while stirring the solution for 30 min.

The reaction medium is concentrated under reduced pressure, the residue is taken up in 200 ml of ice-cold water and is basified by addition of concentrated aqueous sodium hydroxide solution. This mixture is extracted with chloroform and the chloroform extracts are dried and evaporated. The products are obtained as a mixture of diastereoisomers which are separated by chromatography on silica gel, eluting with a 90/10/1 mixture of chloroform, methanol and aqueous ammonia.

2.86 g of the less polar diastereoisomer are thus obtained in the form of a thick oil, $[\alpha]_D^{20} = +48°$ (c=1, MeOH)

and 2.71 g of the more polar diastereoisomer are thus obtained in the form of a thick oil, $[\alpha]_D^{20} = -133.7°$ (c=1, MeOH).

4.5 Hydrochloride (2:1) of (−)-6-pyrrolidin-2-yl-6,7-dihydro-5H-1-pyrindine (Compound No. 4)

2.70 g (9.46 mmol) of the less polar diastereoisomer of (S)-2-(6,7-dihydro-5H-1-pyrindin-6-yl)-1-(pyrrolidin-2-ylcarbonyl)pyrrolidine, obtained in the above step, dissolved in 50 ml of aqueous 6M hydrochloric acid are heated at 100° C. for 48 h in a 100 ml round-bottomed flask. The solution is cooled to room temperature and is basified by addition of concentrated sodium hydroxide solution. This mixture is extracted with chloroform and the extracts are dried and evaporated under reduced pressure. The residue is purified by chromatography on silica gel, eluting with a 90/10/1 mixture of chloroform, methanol and aqueous ammonia. The purified product is treated with 2 equivalents of hydrochloric acid in ethanol. 1.8 g of product are thus obtained in the form of the hydrochloride.

Melting point: 241–242° C.
$[\alpha]_D^{20}=-8.9°$ (c=1, MeOH).

4.6 Hydrochloride (2:1) of (+)-pyrrolidin-2-yl-6,7-dihydro-5H-l-pyrindine (Compound No. 3).

Starting with the more polar diastereoisomer obtained in step 4.4, and working according to the method described in step 4.5, the final compound is obtained in the form of the hydrochloride (2:1).

Melting point: 240–241° C.
$[\alpha]_D^{20}=+7.7°$ (c=1, MeOH)

EXAMPLE 5

(Compounds Nos. 5 and 6)
Hydrochlorides (2:1) of the enantiomers of 6-pyrrolidin-2-yl-6,7-dihydro-5H-1-pyrindine (derived from isomer B).

5.1 Diastereoisomers of (S)-2-((6,7-dihydro-5H-1-pyrindin-6-yl)-1-(pyrrolidin-2-ylcarbonyl)pyrrolidine (derived from isomer B).

Starting with the B isomer obtained in step 4.3, and working according to the method described in step 4.4, the desired compounds are obtained.

Thus, the less polar diastereoisomer is obtained in the form of a thick oil,
$[\alpha]_D^{20}+40.4°$ (c=1, MeOH)
and the more polar diastereoisomer is thus obtained in the form of a thick oil,
$[\alpha]_D^{20}=-118.5°$ (c=1, MeOH).

5.2 Hydrochloride (2:1) of (−)-pyrrolidin-2—yl-6,7-dihydro-5H-1-pyrindine (Compound No. 6).

Starting with the less polar diastereoisomer obtained in step 5.1, and working according to the method described in step 4.5, the final compound is obtained in the form of the hydrochloride (2:1).

Melting point : 223–224° C.
$[\alpha]_D^{20}=-9.1°$ (c=1, MeOH).

5.3 Hydrochloride (2:1) of (+)-pyrrolidin-2-yl-6,7-dihydro-5H-1-pyrindine (Compound No. 5).

Starting with the more polar diaster-oisomer obtained in step 5.1, and working according to the method described in step 4.5, the final compound is obtained in the form of the hydrochloride (2:1).

Melting point: 219–220° C.
$[\alpha]_D^{20}=+6.6°$ (c=1, MeOH)

EXAMPLE 6

(Compound No. 9)
Fumarate (3:2) of (+)-6-(1-methylpyrrolidin-2-yl)-6,7-dihydro-5H-1-pyrindine.

Starting with the hydrochloride (2:1) of (−)-pyrrolidin-2-yl-6,7-dihydro-5H-1-pyrindine obtained in step 5.2, and working according to the method described in Example 2, the final compound is obtained in the form of the fumarate (3:2).

Melting point: 91–93° C.
$[\alpha]_D^{20}=+12.40$ (c=1, MeOH)

EXAMPLE 7

(Compound No. 10)
Fumarate (3:2) of (−)-6-(1-methylpyrrolidin-2-yl)-6,7-dihydro-5H-1-pyrindine.

Starting with the hydrochloride (2:1) of (+)-pyrrolidin-2-yl-6,7-dihydro-5H-1-pyrindine obtained in step 5.3, and working according to the method described in Example 2, the final compound is obtained in the form of the fumarate (3:2).

Melting point: 110–112° C.
$[\alpha]_D^{20}=-10.3°$ (c=1, MeOH).

EXAMPLE 8

(Compound No. 11)
Hydrobromide (2:1) of (±)-4-chloro-6-pyrrolidLn-2-yl-6,7-dihydro-5H-1-pyrindine.

8.1 1,1-Dimethylethyl 2-(6,7-dihydro-5H-pyrindin-6-yl) pyrrolidine-1-carboxylate.

1.3 g (4.68 mmol) of the hydrochloride (2:1) of (±)-6-pyrrolidin-2-yl-6,7-dihydro-5H-1-pyrindine are treated with sodium hydroxide in order to release the base, which is extracted with dichloromethane and the organic phase is dried and the solvent is evaporated off under reduced pressure.

The evaporation residue is dissolved in 20 ml of dichloromethane, 1.08 g (4.98 mmol) of bis(1,1-dimethylethyl dicarbonate are added, the mixture is stirred for 1 h and the solvent is evaporated off under reduced pressure.

1.44 g of compound are obtained, which product is used without further purification in the following step.

8.2 1,1-Dimethylethyl 2-(N-oxide-6,7-dihydro-5H-pyrindin-6-yl)pyrrolidine-1-carboxylate.

1.43 g (4.98 mmol) of 1,1-dimethylethyl 2-(6,7-dihydro-5H-pyrindin-6-yl)pyrrolidine-1 -carboxylate are dissolved in 20 ml of dichlorolnethane, 1.11 g (6.47 mmol) of 3-chloroperbenzoic acid are added and the mixture is stirred for 1 h.

The solvent is evaporated off under reduced pressure, the residue is washed with sodium hydrogencarbonate solution and extracted with dichloromethane, the organic phase is dried and the solvent is evaporated off under reduced pressure. 1.50 g of a thick oil are obtained, which product is used without further purification in the following step.

8.3 Hydrobromide (2:1) of (±)-4-chloro-6-pyrrolidin-2-yl-6,7-dihydro-5H-1-pyrindine.

1.50 g (4.93 mmol) of 1,1-dimethylethyl 2-(N-oxide-6,7-dihydro-5H-pyrindin-6-yl)pyrrolidine-1-carboxylate are dissolved in 21.1 ml of phosphorus oxychloride and the solution is refluxed for 1 h.

The mixture is evaporated to dryness, the residue is taken up in water and aqueous ammonia to pH=10, it is extracted with dichloromethane, the organic phase is filtered, the solvent is evaporated off under reduced pressure and the residue is purified by chromatography on a column of silica gel, eluting with a 90/10 mixture of dichloromethane and methanol. The product is salified with hydrobromic acid and the hydrobromide is recrystallized from a mixture of ethanol and 2-propanol.

0.305 g of compound is obtained.
Melting point: 210° C. (decomposition).

EXAMPLE 9

(Compound No. 12)
Hydrobromide (2:1) of (±)-4-chloro-6-(1-methylpyrrolidin-2-yl)-6,7-dihydro-5H-1-pyrindine.

0.262 g (0.683 mmol) of hydrobromide (2:1) of (+)-4-chloro-6-pyrrolidin-2-yl-6,7-dihydro-5H-1-pyrindine is dissolved in 20 ml of ethanol, 102 Al (1.37 mmol) of 37% formaldehyde are added, followed by 78.2 µl (1.37 mmol) of acetic acid and then, at 0° C. and under an argon atmosphere, 86 mg (1.37 mmol) of sodium cyanoborohydride are added and the mixture is stirred for 2 h.

The mixture is concentrated to dryness, the residue is taken up in water and then sodium hydroxide to pH=10 and the mixture is extracted with dichloromethane.

The organic phase is dried and the solvent is evaporated off under reduced pressure. 0.167 g of product is obtained, which is purified by thin layer chromatography.

0.133 g of base is obtained, which is treated with hydrobromic acid in the presence of acetic acid, and 0.224 g of hydrobromide is finally isolated.

Melting point: 220° C. (decomposition).

EXAMPLE 10
(Compounds Nos. 13 and 14)

Hydrobromide (2:1) of (+)-2-chloro-6-pyrrolidin-2-yl-6,7-dihydro-5H-1-pyrindine.

10.1 6-Chloropyridine-2,3-dicarboxylic acid. (cf. J. Org. Chem. (1990) 55 1928–1932).

1596 g (7 mol) of periodic acid are dissolved in 1 l of water, 1 l of acetonitrile, followed by 80.67 g (0.493 mol) of 2-chloroquinoline dissolved in 1 l of carbon tetrachloride are added.

The homogeneous two-phase mixture is stirred and 2.04 g (9.86 mmol) of ruthenium chloride are added. The reaction is exothermic and causes refluxing of the carbon tetrachloride for more than one hour. The mixture is allowed to return to room temperature and is left to stand overnight.

The mixture is filtered through paper, the aqeuous phase is separated out after settling of the phases has taken place and is extracted several times with ethyl acetate, and the organic phases axe combined. After washing with water, drying over sodium sulphate and evaporation of the solvent under reduced pressure, 59.78 g of compound are isolated.

Melting point: 139.5° C.

10.2 Diethyl 6-chloropyridine-2,3-dicarboxylate.

11 g (54.6 mmol) of 6-chloropyridine-2,3-dicarboxylic acid are dissolved in 70 ml of ethanol, the solution is cooled to 4° C., 8 ml (109 mmol) of thionyl chloride are added dropwise and the mixture is allowed to return to room temperature and is heated at reflux for 5 h. The solvent is evaporated off under reduced pressure, the residue is taken up in 100 ml of water, potassium carbonate is added to pH=8 and the mixture is extracted with dichloromethane. After washing, drying and evaporation of the solvent, 13.7 g of compound are obtained, which product is used without further purification in the following step.

10.3 6-Chloropyridine-2,3-dimethanol.

13.56 g (52.6 mmol) of diethyl 6-chloropyridine-2,3-dicarboxylate are dissolved in 100 ml of ethanol, the solution is cooled to 3° C., 4 g (105 mmol) of sodium borohydride are added, followed by portionwise addition of 5.84 g (52.6 mmol) of calcium chloride, while monitoring the temperature. The mixture is allowed to return'to room temperature and stirring is continued for 24 h.

The mixture is cooled to 3° C., a solution of 4 ml of concentrated sulphuric acid in 36 ml of water is added, the mixture is stirred for 30 min, it is filtered, rinsing the precipitate with ethanol, concentrated sodium hydroxide is added to the filtrate to pH=10, this mixture is concentrated under reduced pressure, the residue is taken up in ethanol, the mixture is filtered and the filtrate is concentrated under reduced pressure.

6.11 g of compound are obtained.

Melting point: 368–369° C.

10.4 6-Chloro-2,3-di(chloromethyl)pyrindine.

5.45 g (31.4 mmol) of 6-chloropyridine-2,3-dimethanol are added to 35 ml of thionyl chloride and the mixture is stirred at room temperature for 3 h and then at reflux for 3 h.

The mixture is allowed to cool, it is poured onto ice and neutralized with concentrated sodium hydroxide, this mixture is extracted with dichloromethane, the organic phase is washed, dried over sodium sulphate and the solvent is evaporated off under reduced pressure. 4.79 g of compound are obtained in the form of an oil.

10.5 Diethyl 2-chloro-6,7-dihydro-5H-1-pyrinciine-6,6-dicarboxylate.

1.03 g (44.6 mmol) of sodium are dissolved in 60 ml of ethanol, 3.58 g (22.3 mmol) of diethyl malonate are added, the mixture is stirred for 5 min, it is cooled to +2° C. and 4.7 g of 6-chloro-2,3-di(chloromethyl)pyrindine dissolved in 45 ml of ethanol are added slowly. The mixture is allowed to return to room temperature and the stirring is maintained for 4 h.

The solvent is evaporated off under reduced pressure, the residue is taken up in water, this mixture is extracted with dichloromethane, and the organic phase is washed, dried over sodium sulphate and the solvent is evaporated off under reduced pressure.

6.4 g of compound are obtained in the form of an oil.

10.6 Hydrobromide (2:1) of (+)-2-chloro-6-pyrrolidin-2-yl-6,7-dihydro-5H-1-pyrindine.

2-Chloro-6,7-dihydro-5H-1-pyrindine-6-carboxylic acid is prepared under conditions similar to those described in step 1.2, after which the process is performed under conditions similar to those described in steps 4.1 to 4.3.

Melting points: 200–203° C. (A isomer)

224–225° C. (B isomer).

EXAMPLE 11
(Compounds Nos. 17 and 18)

Hydrobromide (2:1) of (±)-2-methoxy-6-pyrrolidin-2-yl-6,7-dihydro-5H-1-pyrindine.

11.1 Dimethyl 6-chloropyridine-2,3-dicarboxylate.

Starting with 59.3 g (0.294 mol) of 6-chloropyridine-2,3-dicarboxylic acid, 500 ml of methanol and 47 ml of thionyl chloride, and working under conditions similar to those'described in step 10.2, 64.8 g of diester are obtained.

11.2 Dimethyl 6-methoxypyridine-2,3-dicarboxylate.

6.1 g (0.265 mol) of sodium are dissolved in 300 ml of methanol, 47 g (0.205 mol) of methyl 6-chloropyridine-2,3-dicarboxylate dissolved in 100 ml of methanol are added and the mixture is reflaxed for 1 h. The sodium chloride is separated out by filtration, a few pieces of cardice are added, with caution, to saturate the mixture with carbon dioxide, the solvent is evaporated off under reduced pressure, the residue is triturated in 100 ml of water and the solid is collected by filtration, washed with water and dried.

39.3 g of compound are obtained.

Melting point: 56–59° C.

11.3 6-Methoxypyridine-2,3-di(methanol).

39 g (0.173 mol) of dimethyl 6-methoxy pyridine-2,3-dicarboxylate are dissolved in 1 l of diethyl ether, 13.14 g (0.346 mol) of lithium aluminium hydride are added slowly, while maintaining the temperature below 30° C., after which the mixture is left stirring for 1 h 30. Saturated aqueous sodium sulphate solution is added, while cooling the mixture to 4° C. until the evolution of gas has ceased, and stirring is continued under cold conditions for 1 h 30.

The mixture is filtered, rinsing the solid with methanol, and the solvents are evaporated off under reduced pressure.

11.4 Hydrobromide (2:1) of (+)-2-methoxy-6-pyrrolidin-2-yl-6,7-dihydro-5H-1-pyrindine.

Starting with 6-methoxypyridine-2,3-di(methanol) and working under similar conditions to those of Examples 10.4 to 10.6.

Melting points: 208–209° C. (A isomer)

172–174° C. (B isomer).

The table which follows illustrates the chemical structures and the physical properties of a number of compounds according to the invention.

TABLE

| No. | R₁ | R₃ | R₅ | Stereochemistry | Comments | Salt | m.p. (° C.) | $[\alpha]_D^{20}$ (°) |
|---|---|---|---|---|---|---|---|---|
| 1 | H | H | H | (±) | A isomer | HCl 2:1 | 228–229 | — |
| 2 | H | H | H | (±) | B isomer | HCl 2:1 | 176–177 | — |
| 3 | H | H | H | (±) enantiomer of No. 1 | derived from the A isomer | HCl 2:1 | 240–241 | +7.7 |
| 4 | H | H | H | (−) enantiomer of No. 1 | | HCl 2:1 | 241–242 | −8.9 |
| 5 | H | H | H | (+) enantiomer of No. 2 | derived from the B isomer | HCl 2:1 | 219–220 | +6.6 |
| 6 | H | H | H | (−) enantiomer of No. 2 | | HCl 2:1 | 223–224 | −9.1 |
| 7 | CH₃ | H | H | (±) | derived from No. 1 | HCl 2:1 | 87–89 | — |
| 8 | CH₃ | H | H | (±) | derived from No. 2 | Fum. 2:1 | 116–118 | — |
| 9 | CH₃ | H | H | (+) enantiomer of No. 8 | derived from No. 6 | Fum. 3:2 | 91–93 | +12.4 |
| 10 | CH₃ | H | H | (−) enantiomer of No. 8 | derived from No. 5 | Fum. 3:2 | 110–112 | −10.3 |
| 11 | H | H | Cl | (±) | B isomer | HBr 2:1 | 210 (d) | — |
| 12 | CH₃ | H | Cl | (±) | B isomer | HBr 2:1 | 220 (d) | — |
| 13 | H | Cl | H | (±) | A isomer | HBr 2:1 | 200–203 | — |
| 14 | H | Cl | H | (±) | B isomer | HBr 2:1 | 224–225 | — |
| 15 | CH₃ | Cl | H | (±) | A isomer | HBr 2:1 | oil | — |
| 16 | CH₃ | Cl | H | (±) | B isomer | HCl 1:1 | 131–134 | — |
| 17 | H | OCH₃ | H | (±) | A isomer | HBr 2:1 | 208–209 | — |
| 18 | H | OCH₃ | H | (±) | B isomer | HBr 2:1 | 172–174 | — |

In the "salt" column, "—" denotes a compound in base form, "HCl" denotes a hydrochloride, "HBr" denotes a hydrobromide and "Fum." denotes a fumarate, or (E)-2-butenedioate; the acid:base molar ratios are indicated in this same column.
In the "m.p. (° C.)" column, "(d)" denotes a melting point with decomposition.
In the $[\alpha]_D^{20}$ column, the optical rotations are indicated for c = 1, MeOH.

The compounds of the invention underwent tests which revealed their therapeutic properties.

Thus, they were studied as regards their affinity towards nicotinic receptors, according to the methods described by Anderson and Arneric, *Eur. J. Pharmacol* (1994) 253 261, and by Hall et al., *Brain Res.* (1993) 600 127.

Male Sprague Dawley rats weighing 150 to 200 g are decapitated and the entire brain is removed rapidly, it is homogenized in 15 volumes of 0.32M sucrose solution at 4° C. and is then centrifuged at 1000×g for 10 min. The pellet is discarded and the supernatant is centrifuged at 20,000×g for 20 min at 4° C. The pellet is collected and homogenized using a Polytron™ mill in 15 volumes of double-distilled water at 4° C., after which it is centrifuged at 8000×g for 20 min. The pellet is discarded and the supernatant and the layer of skin ("buffy coat") are centrifuged at 4000×g for 20 min, the pellet is recovered, washed with double-distilled water at 4° C. and centrifuged once again before being stored at −80° C.

On the day of the experiment, the tissue is thawed slowly and is suspended in 3 volumes of buffer. 150 µl of this membrane suspension are incubated at 4° C. for 120 min in the presence of 100 µl of 1 nM [³H]cytisine in a final volume of 500 µl of buffer, in the presence or absence of test compound. The reaction is quenched by filtration through Whatman GF/B™ filters pretreated with polyethyleneimine, the filters are rinsed with twice 5 ml of buffer at 4° C. and the radioactivity retained on the filter is measured by liquid scintigraphy. The non-specific binding is determined in the presence of 10 µm (−)-nicotine; the non-specific binding represents 75 to 85% of the total binding recovered on the filter. For each concentration of test compound, the percentage of inhibition of the specific binding of [³H]cytisine is determined, then the $IC_{50}$, the concentration of compound which inhibits 50% of the specific binding, is calculated. The $IC_{50}$ values for the compounds of the invention are between 0.001 and 1 µM.

The results of the biological tests carried out on the compounds of the invention show that they are powerful and selective cholinergic ligands for nicotinic receptors.

These results suggest the use of the compounds in the treatment or prevention of disorders associated with dysfunctioning of the nicotinic receptors, in particular in the central nervous system or in the gastrointestinal system.

In the central nervous system, these disorders comprise cognitive deficiencies, more specifically memory deficiencies, but also attention deficiencies, associated with Alzheimer's disease, with pathological ageing (Age-Associated Memory Impairment, AAMI), with Parkinson's disease, with trisomy 21 (Down's syndrome), with Korsakoff's alcoholic syndrome and with vascular dementia (multi-infarct dementia, MID).

The compounds of the invention may also be useful in the treatment of motor disorders observed in Parkinson's disease or other neurological diseases such as Huntington's chorea, Tourette's syndrome, tardive dyskinesia and hyperkinesia.

The compounds of the invention can also constitute a curative or symptomatic treatment of cerebrovascular accidents and cerebral hypoxic attacks. They can be used in cases of psychiatric pathology: schizophrenia, depression, anxiety, panic attacks, compulsive and obsessive behaviour. They can prevent the symptoms due to withdrawal from tobacco, from alcohol or from the various substances which induce a dependency, such as cocaine, LSD, cannabis or benzodiazepines. Lastly, they can be useful for the treatment of pain.

In the gastrointestinal system, the compounds of the invention may be useful in the treatment of Crohn's disease, ulcerous colitis, irritable bowel syndrome and obesity.

To this end, the compounds of the invention can be in any composition form which is suitable for enteral, parenteral or transdermal administration, such as tablets, coated tablets, gelatin capsules, wafer capsules, drinkable or injectable suspensions or solutions such as syrups or ampules, transdermal patches, etc., combined with suitable excipients, and dosed to allow a daily administration of from 0.01 to 20 mg/kg.

What is claimed is:

1. A compound of formula (I),

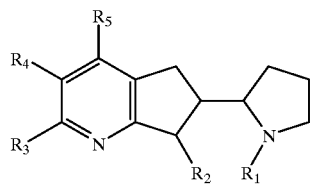

(I)

in the form of a pure oDtical isomer, or a mixture of compounds of: formula (I) in the forms of different optical isomers,
in which
$R_1$ represents a hydrogen atom, a $(C_1-C_4)$ alkyl group or a phenyl $(C_1-C_4)$ alkyl group,
$R_2$ represents a hydrogen atom or a $(C_1-C_4)$ alkyl group, and
$R_3$, $R_4$ and $R_5$ each represent, independently of each other, a hydrogen or halogen atom or a trifluoromethyl, cyano, hydroxyl, $(C_1-C_6)$ alkyl or $(C_1-C_6)$ alkoxy group, in the form of the base or of an addition salt with an acid.

2. A process for the preparation of a compound according to claim 1, which comprises reducing an imine of general formula (V)

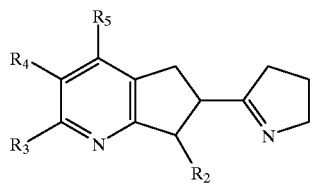

(V)

in which $R_2$, $R_3$, $R_4$ and $R_5$ are as defined in claim 1, to a derivative of general formula (VI)

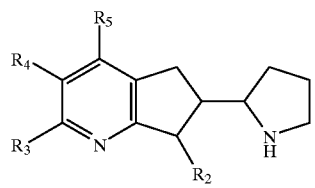

(VI)

and then, if so desired, separating the stereoisomers and/or the enantiomers of this derivative, and finally, if it is desired to introduce a group $R_1$ which is other than a hydrogen atom, alkylating the nitrogen of the pyrrolidine ring.

3. A pharmaceutical composition, which comprises an effective amount of a compound according to claim 1 and an excipient.

4. A method for the treatment of a disorder associated with the disfunctioning of nicotinic receptors, which comprises administering to a host in need of the treatment therapeutically an effective amount of a compound as claimed in claim 1.

5. A method as claimed in claim 4, wherein the disorder is a disorder in the central nervous system or gastrointestinal system.

6. A method as claimed in claim 4, wherein the disorder is a cognitive deficiency.

7. A method as claimed in claim 6, wherein the disorder is a memory deficiency or attention deficiency.

8. A method as claimed in claim 4, wherein the disorder is a motor disorder.

9. A method as claimed in claim 4, wherein the disorder is schizophrenia, depression, anxiety, panic attack, compulsive and obsessive behavior, or withdraw from tobacco, alcohol or other substance that induces a dependency.

10. A method as claimed in claim 4, wherein the disorder is Crohn's disease, ulcerous colitis, irritable bowel syndrome, or obesity.

* * * * *

UNITED STATES PATENT AND TRADEMARK OFFICE
CERTIFICATE OF CORRECTION

PATENT NO. : 6,184,229 B1
DATED : February 6, 2001
INVENTOR(S) : Alistair Lochead et al It is certified that error appears in the above-identified patent and that said Letters Patent is hereby corrected as shown below:

Cover page, insert --(30) Foreign Application Priority Data
July 9, 1997 (FR) 9708706--.

Claim 1, column 13, line 17, "oDtical" should read --optical--;

Claim 1, column 13, line 18, after "compounds of", delete ":".

Claim 4, column 14, line 23, before "effective", delete "an".

Signed and Sealed this

Fifteenth Day of May, 2001

*Attest:*

NICHOLAS P. GODICI

*Attesting Officer*     Acting Director of the United States Patent and Trademark Office